United States Patent
Cao et al.

(10) Patent No.: US 11,237,160 B2
(45) Date of Patent: *Feb. 1, 2022

(54) ULTRASENSITIVE SENSOR BASED ON A PIEZOELECTRIC TRANSISTOR

(71) Applicant: INTERNATIONAL BUSINESS MACHINES CORPORATION, Armonk, NY (US)

(72) Inventors: Qing Cao, Westchester, NY (US); Jianshi Tang, Elmsford, NY (US); Ning Li, White Plains, NY (US); Ying He, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 246 days.

This patent is subject to a terminal disclaimer.

(21) Appl. No.: 16/413,116

(22) Filed: May 15, 2019

(65) Prior Publication Data
US 2019/0265181 A1    Aug. 29, 2019

Related U.S. Application Data

(63) Continuation of application No. 15/846,915, filed on Dec. 19, 2017, now Pat. No. 10,352,888.

(51) Int. Cl.
*G01N 33/543* (2006.01)
*G01N 27/07* (2006.01)
*H01L 41/187* (2006.01)
*H01L 41/23* (2013.01)
*H01L 41/314* (2013.01)
(Continued)

(52) U.S. Cl.
CPC ......... *G01N 33/5438* (2013.01); *G01N 27/07* (2013.01); *H01L 41/18* (2013.01); *H01L 41/1875* (2013.01); *H01L 41/23* (2013.01); *H01L 41/29* (2013.01); *H01L 41/314* (2013.01)

(58) Field of Classification Search
CPC ............... G01N 33/5438; G01N 27/07; H01L 41/1875; H01L 41/23; H01L 41/314; H01L 41/29; H01L 41/18
See application file for complete search history.

(56) References Cited

U.S. PATENT DOCUMENTS

| | | | | |
|---|---|---|---|---|
| 5,120,505 A * | 6/1992 | Lowell, Jr. | ............. | G01N 19/00 422/82.01 |
| 6,275,020 B1 * | 8/2001 | Nagano | ................ | G01R 23/173 324/76.19 |

(Continued)

FOREIGN PATENT DOCUMENTS

CN    105953821 B *  9/2016  ............... G01D 5/12

OTHER PUBLICATIONS

U.S. Office Action issued in U.S. Appl. No. 16/413,149 dated Jun. 15, 2021, pp. 1-20.

(Continued)

*Primary Examiner* — Melanie Brown
(74) *Attorney, Agent, or Firm* — Tutunjian & Bitetto, P.C.; Stosch Sabo

(57) ABSTRACT

Chemical sensors include a functionalized electrode configured to change surface potential in the presence of an analyte. A piezoelectric element is connected to the functionalized electrode. A piezoresistive element is in contact with the piezoelectric element.

14 Claims, 5 Drawing Sheets

(51) Int. Cl.
*H01L 41/29* (2013.01)
*H01L 41/18* (2006.01)

(56) References Cited

U.S. PATENT DOCUMENTS

| | | |
|---|---|---|
| 8,159,854 B2 | 4/2012 | Elmegreen et al. |
| 8,519,449 B2 | 8/2013 | Dumitru et al. |
| 8,628,477 B2 | 1/2014 | Addison et al. |
| 8,828,713 B2 | 9/2014 | Ren et al. |
| 9,425,381 B2 | 8/2016 | Elmegreen et al. |
| 9,590,167 B2 | 3/2017 | Elmegreen et al. |
| 9,679,645 B2 | 6/2017 | Elmegreen et al. |
| 2008/0090259 A1* | 4/2008 | Toone .................. G01N 33/543 435/7.25 |
| 2011/0138916 A1* | 6/2011 | Mutharasan ........... G01H 13/00 73/579 |
| 2012/0137783 A1* | 6/2012 | Wang ..................... B82Y 30/00 73/717 |
| 2014/0300251 A1* | 10/2014 | Colli ....................... G06F 1/163 310/339 |
| 2015/0255699 A1* | 9/2015 | Elmegreen .............. H01L 49/00 310/366 |
| 2016/0169834 A1 | 6/2016 | Ning et al. |

OTHER PUBLICATIONS

Mastura Shafinaz Zainal Abidin et al., Open-Gated pH Sensor Fabricated on an Undoped-AlGaN/GaN HEMT Structure, Sensors, Mar. 2011.

B.S. Kang et al., Role of Gate Oxide in AlGaN/GaN High-Electron-Mobility Transistor pH Sensors, Journal of Electronic Materials, Sep. 2007.

I.-B Magdau et al., The piezoelectronic stress transduction switch for very large-scale integration, low voltage sensor computation, and radio frequency applications, Applied Physics Letters, Jun. 2015.

* cited by examiner

ULTRASENSITIVE SENSOR BASED ON A PIEZOELECTRIC TRANSISTOR

BACKGROUND

Technical Field

The present invention generally relates to chemical and biological sensors and, more particularly, to sensors that are triggered using piezoelectric transistors with subthreshold swing below 60 mV/dec.

Description of the Related Art

Transistors (including field effect transistors (FETs) and bipolar junction transistors (BJTs)) can be used as sensors in chemical and biological testing scenarios. The presence of a particular chemical species being measured (referred to herein as an "analyte") causes a charge or voltage to build up on the gate or the base terminal of the transistor, thereby changing the amount of current passing through the device and providing a detection signal.

However, such sensors have limited sensitivity, limited by a transistor's sub-threshold slope. The sub-threshold slope characterizes how the device's effective resistance changes for voltages below the transistor's threshold voltage. Such devices generally exhibit exponentially increasing current as voltage increases in the sub-threshold range, and the sub-threshold slope is measured in units of millivolts per order of magnitude change in the output current. Typical transistors have a sub-threshold slope of about 60 mV/decade.

SUMMARY

A chemical sensor includes a functionalized electrode configured to change surface potential in the presence of an analyte. A piezoelectric element is connected to the functionalized electrode. A piezoresistive element is in contact with the piezoelectric element.

A chemical sensor includes a functionalized electrode configured to change surface potential in the presence of an analyte. A piezoelectric element is connected to the functionalized electrode. A piezoresistive element is in contact with the piezoelectric element. An input terminal is in contact with the piezoresistive element. An output terminal in contact with the piezo resistive element and the piezoelectric element, between the piezoelectric element and the piezoresistive element.

A chemical sensor includes a functionalized electrode configured to change surface potential in the presence of an analyte. A piezoelectric element is connected to the functionalized electrode. A piezoresistive element is in contact with the piezoelectric element. A sensor analysis system is configured to measure a current through the piezoresistive element and to compare the measured current to a calibration curve of predetermined concentrations of the analyte to determine an analyte concentration that corresponds to the measured current.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention provide sensors with superior sensitivity using piezoelectric and piezoresistive structures to achieve a lower subthreshold slope, such that small changes in voltage will trigger a large change in measured current. To accomplish this, a relatively large piezoelectric structure is used to sense voltage changes, which causes a change in the volume of the piezoelectric structure. A piezoresistive structure in contact with the piezoelectric structure is thereby put under strain, and this strain results in a change in the resistance of the piezoresistive structure.

Figure 1:
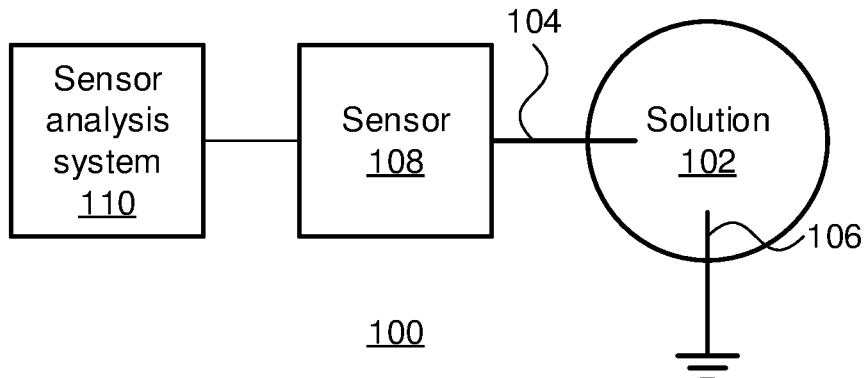
FIG. 1 is a block diagram of a chemical sensor system that uses a piezoelectric/piezoresistive sensor in accordance with an embodiment of the present invention.

Referring now to FIG. 1, a sensor system 100 is shown. The system 100 includes a solution 102 that is being tested for the presence of an analyte. A functionalized metal electrode 104 is present in the solution 102 along with a grounded reference electrode 106. The functionalized metal electrode 104 has a treatment or composition that binds to the analyte in question, such that the analyte adsorbs to the surface of the functionalized metal electrode 104 and changes the surface potential. It should be understood that, although the present embodiments are described with respect to a liquid solution, the same principles may also be applied to sensors configured to detect gaseous analytes. A "functionalized" metal is a material that has chemicals on its surface that selectively bind with a specific analyte. The chemicals may include any appropriate substance from small molecules to large biomolecules, such as enzymes, antibodies, and aptamers. In one specific embodiment, the material of the reference electrode 106 may be made up of a silver wire immersed in a saturated silver chloride solution with a fixed potential. Thus, measuring the voltage difference between the reference electrode 106 and the functionalized metal electrode 104 can provide an absolute potential on the sensing electrode.

The functionalized metal electrode, in turn, is connected to the sensor device 108. As is discussed in greater detail below, the sensor device 108 makes use of a transistor-like device. A change in the surface potential of the functionalized electrode 104 causes a corresponding change in the potential at a piezoelectric element of the sensor device 108 which, in turn, triggers a change in resistance in a piezoresistive device in the sensor device 108, thereby changing a current output by the sensor device 108. A sensor analysis system 110 monitors current output by the sensor 108, maintaining a record of the sensor's output to determine when that output changes, indicating the presence of an analyte.

In one specific example, where the sensor system 100 is used to detect a pH change, the functionalized metal electrode 104 may be functionalized by titanium nitride. The pH level of the solution 102 affects the surface potential at the functionalized metal electrode 104, with different pH values being associated with different potentials. Because the subthreshold slope of the sensor device 108 is low, a small change in pH will result in a large change in output current, making even small pH changes easy to measure.

Figure 2:
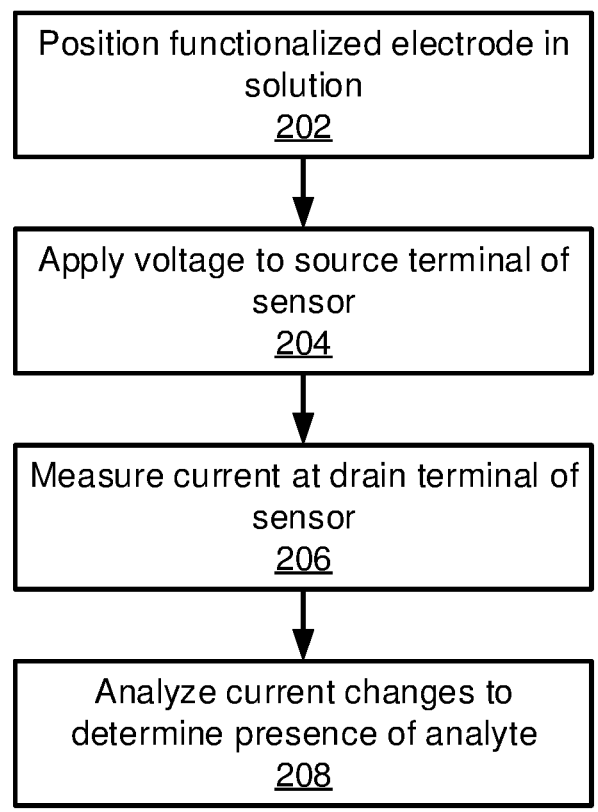
FIG. 2 is a block/flow diagram of a method of detecting the presence of an analyte using a piezoelectric/piezoresistive sensor in accordance with an embodiment of the present invention.

Referring now to FIG. 2, a method for detecting the presence of an analyte is shown. Block 202 positions the functionalized electrode 104 in the solution 102, which generates a voltage at the piezoelectric element of the sensor 108. Block 204 applies a voltage to the piezoresistive element of the sensor 108 and block 206 measures the resulting current. Block 208 analyzes the current output by the sensor 108. This analysis looks for changes in the current as well as its absolute value. The output current is directly proportional to the amount of analyte present.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 3:
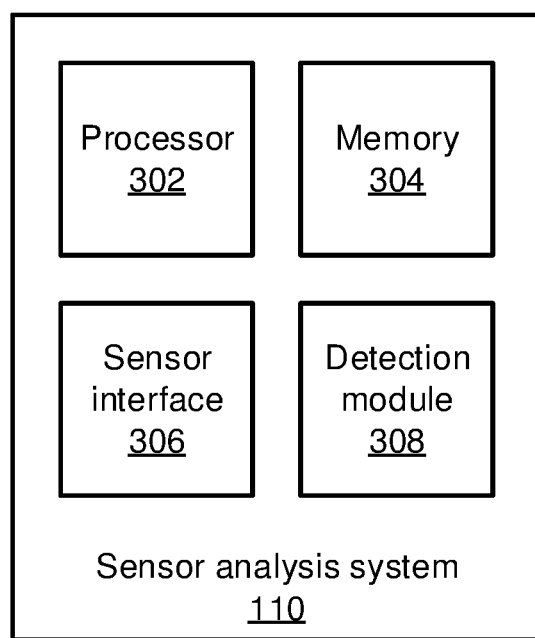
FIG. 3 is a block diagram of a sensor analysis system for detecting he presence of an analyte using a piezoelectric/piezoresistive sensor in accordance with an embodiment of the present invention.

Referring now to FIG. 3, additional detail on the sensor analysis system 110 is shown. The sensor analysis system 110 includes a hardware processor 302 and a memory 304. A sensor interface 306 collects current measurements from the sensor 108 and may include, for example, an ammeter. The sensor interface 306 stores sensor values in the memory 304. A detector module 308 is configured to detect changes in the sensor values by, e.g., comparison to values stored in the memory 304. The detector module 308 may then provide some indication of the detection of an analyte by, e.g., providing a visual or audio indication.

The detector module 308 may, in particular, make use of a calibration curve stored in the memory 304. The calibration curve establishes correspondences between previously measured currents and known concentrations of the analyte. In such an embodiment, the detector module 308 can compare a current value provided by the sensor interface 306 to the calibration curve to determine a corresponding analyte concentration. The calibration curve may include interpolated points between those points actually measured for respective known analyte concentrations, such that the detector module 308 can provide a concentration measurement even for concentrations that were not explicitly measured during calibration.

Figure 4:
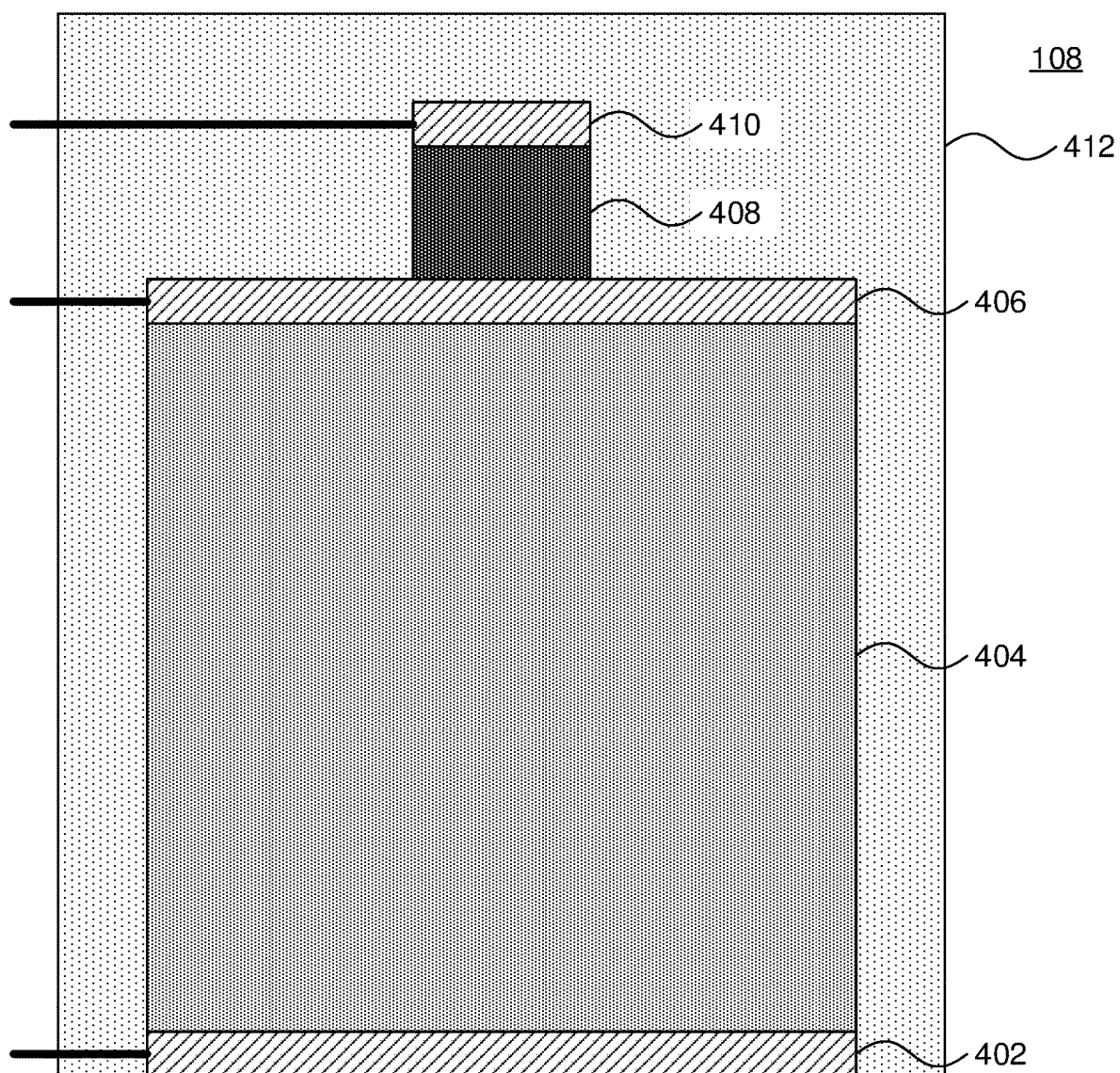
FIG. 4 is a cross-sectional diagram showing a piezoelectric/piezoresistive sensor in accordance with an embodiment of the present invention.

Referring now to FIG. 4, additional detail on the sensor 108 is shown. A piezoelectric element 404 and a piezoresistive element 408 are shown. The piezoelectric element 404 has a large size relative to the piezoresistive element 408. Three terminals are also shown, with a first terminal 402 being connected to the functionalized electrode 108, a second terminal 406 being connected to ground, and a third terminal 410 being connected to a constant voltage source.

It is contemplated that the piezoelectric element 404 may be formed from any appropriately sensitive piezoelectric material. Examples of such piezoelectric materials include, e.g., $(1-x)[Pb(Zn_{1/3}Nb_{2/3})O_3]-x[PbTiO_3]$ and $(1-x)[Pb(Mg_{1/3}Nb_{2/3})O_3]-x[PbTiO_3]$. The piezoresistive element 408 may similarly be formed from any appropriately sensitive piezoresistive material having a continuous transition between metal and insulator under changes in pressure. Examples of such piezoresistive materials include, e.g., SmSe, TmTe, and chromium-doped $V_2O_3$.

As the voltage on the first terminal 402 changes in the presence of an analyte, the piezoelectric element 404 changes its physical volume. The piezoelectric effect describes the interaction between the mechanical state and electrical state of a material. It is a reversible process where an applied voltage causes a change in the physical size or shape of the material. Similarly, a pressure or strain applied to a piezoelectric material will generate a voltage at the surface of the material. The piezoelectric element 404 is formed with a relatively large size, so that the applied voltage will cause a proportionally larger change in volume.

The physical changes from the piezoelectric element 404 apply a strain (either pushing or pulling) on the piezoresistive element 408. This triggers the piezoresistive properties of the piezoresistive element 408. The piezoresistive effect describes the interaction between an applied strain and the electrical resistance demonstrated by that material. Thus, as the piezoelectric 404 applies a strain, the piezoresistive element 408 changes its resistance accordingly. In general, the piezoresistive effect follows the relationship:

$$\varepsilon \rho_\sigma = \left(\frac{\partial \rho}{\rho}\right)$$

where ε is the strain, $\rho_\sigma$ is a piezoresistive coefficient that characterizes the material, $\partial \rho$ is a change in resistivity, and ρ is the rest-state resistivity with no strain applied. Thus, as the sensor analysis system 110 measures the current passing between the third terminal 410 and the grounded second terminal 406, this relationship is used to determine the present resistivity of the piezoresistive element 408, which determines the strain applied to the piezoresistive element 408 by the piezoelectric element 404, which in turn determines the voltage being applied to the piezoelectric element 404, and hence the concentration of the analyte at the functionalized electrode 104.

In some embodiments, the actual voltages and the actual resistances need not be known or measured. In such embodiments, the sensor 108 is calibrated with a set of known concentrations of the analyte to generate a characteristic current/concentration curve that maps out how the sensor 108 will react in concentrations. The concentration of a test solution can then be determined by simply measuring the current and comparing the measured current to the characteristic curve.

It should be noted that the sensor 108 is encapsulated in a passivating layer 412. This passivating layer 412 performs a dual role of preventing electrical shorts and of proving a "backstop" for the piezoresistive element 408. Thus, as the piezoelectric element 404 applies a pressure on the piezoresistive element 408, the piezoresistive element 408 is prevented from moving away and instead experiences the increased strain that causes a change in its resistivity. It is specifically contemplated that the passivating layer 412 may be formed from, e.g., silicon dioxide, but it should be understood that any appropriate dielectric material may be used instead.

Figure 5:
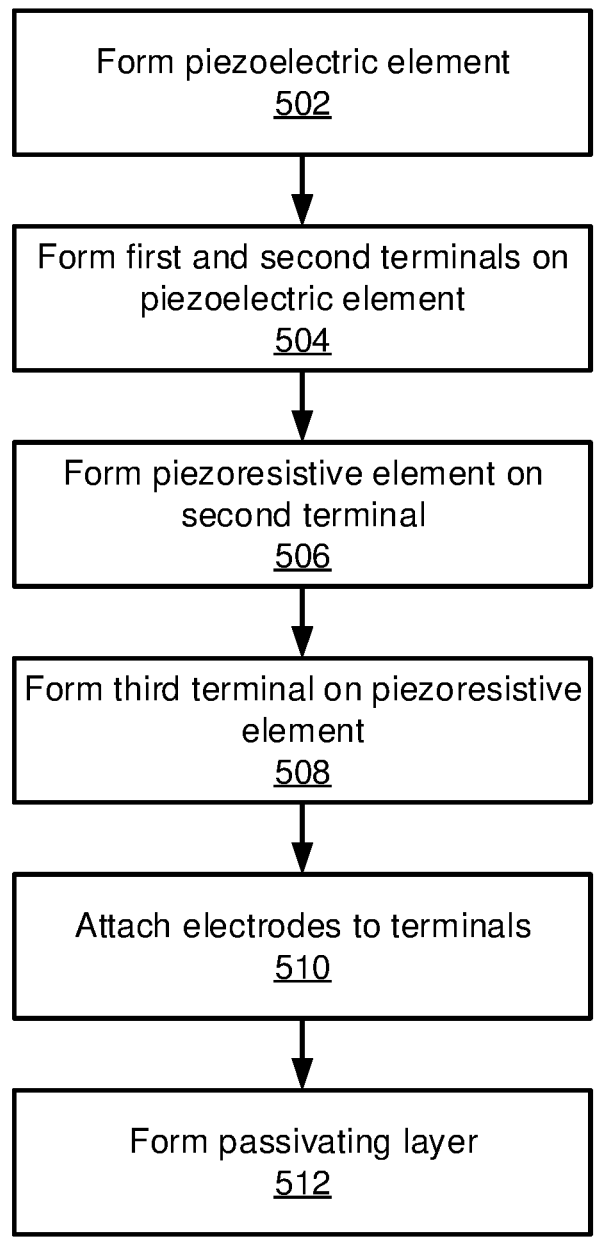
FIG. 5 is a block/flow diagram of a method of forming a piezoelectric/piezoresistive sensor in accordance with an embodiment of the present invention.

Referring now to FIG. 5, a method of forming a sensor 108 is shown. It should be understood that, although the present process is presented in an ordered fashion, the piezoelectric and piezoresistive layers may be formed in a reverse order or simultaneously, with the terminals and passivating layer being formed at any appropriate time.

Block 502 forms the piezoelectric element 404 by any appropriate process. For example, a piezoelectric thin film 404 can be deposited by pulsed laser deposition with a lead-enriched ceramic target. A pulsed laser beam to be used for this purpose may be generated by a krypton-fluoride laser having an output wavelength of about 248 nm. Block 504 then forms first terminal 402 and second terminal 406 on the piezoelectric element 404 by any appropriate deposition process including, e.g., chemical vapor deposition (CVD), physical vapor deposition (PVD), atomic layer deposition (ALD), gas cluster ion beam (GCIB) deposition, electroplating, etc.

The gate dielectric layer 502 may be formed by any appropriate process including, e.g., chemical vapor deposition (CVD), physical vapor deposition (PVD), atomic layer deposition (ALD), or gas cluster ion beam (GCIB) deposition. CVD is a deposition process in which a deposited species is formed as a result of chemical reaction between gaseous reactants at greater than room temperature (e.g., from about 25° C. about 900° C.). The solid product of the reaction is deposited on the surface on which a film, coating, or layer of the solid product is to be formed. Variations of CVD processes include, but are not limited to, Atmospheric Pressure CVD (APCVD), Low Pressure CVD (LPCVD), Plasma Enhanced CVD (PECVD), and Metal-Organic CVD (MOCVD) and combinations thereof may also be employed. In alternative embodiments that use PVD, a sputtering apparatus may include direct-current diode systems, radio frequency sputtering, magnetron sputtering, or ionized metal plasma sputtering. In alternative embodiments that use ALD, chemical precursors react with the surface of a material one at a time to deposit a thin film on the surface. In alternative embodiments that use GCIB deposition, a high-pressure gas is allowed to expand in a vacuum, subsequently condensing into clusters. The clusters can be ionized and directed onto a surface, providing a highly anisotropic deposition.

Block 506 then forms piezoresistive element 408 on the second terminal 406. The piezoresistive layer may be deposited using PVD by co-sputtering from, e.g., samarium and selenium sources in a high vacuum system with a base pressure on the order of about $10^{-9}$ Torr. Block 508 then forms the third terminal 410 on the piezoresistive element 408, again by any appropriate deposition process.

Block 510 attaches electrodes to the terminals and block 512 forms the passivating layer 412. The passivating layer may be formed from any appropriate dielectric material, such as silicon dioxide, and may be formed by any appropriate process including, e.g., CVD, ALD, PVD, GCIB deposition, or a spin-on flowable oxide deposition process.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-31\ x}$, where x is less than or equal to 1, etc. In addition, other elements can be included in the compound and still function in accordance with the present principles. The compounds with additional elements will be referred to herein as alloys.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Figure 6:
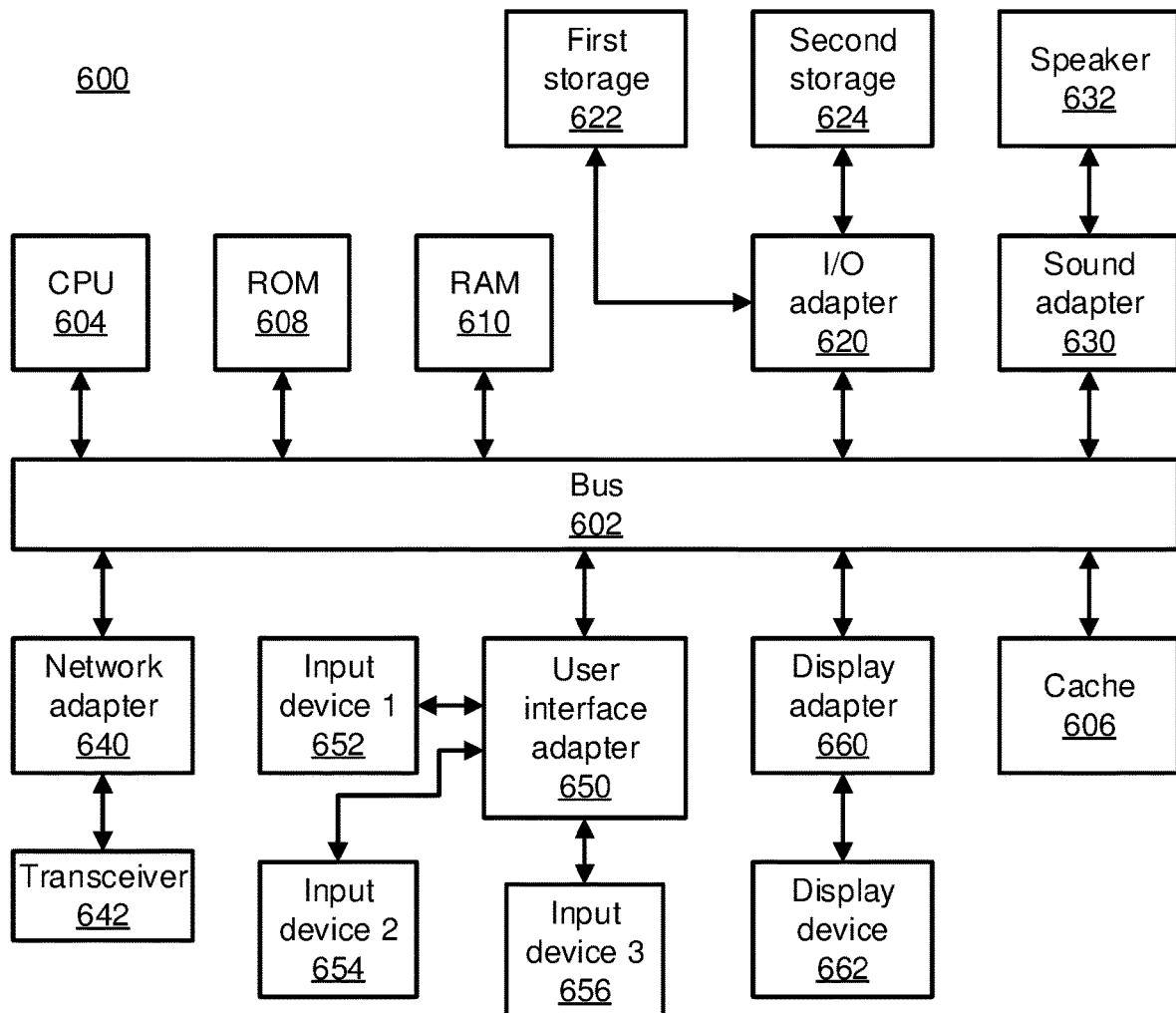
FIG. 6 is a processing system in accordance with an embodiment of the present invention.

Referring now to FIG. 6, an exemplary processing system 600 is shown which may represent sensor analysis system 110. The processing system 600 includes at least one processor (CPU) 604 operatively coupled to other components via a system bus 602. A cache 606, a Read Only Memory (ROM) 608, a Random Access Memory (RAM) 610, an input/output (I/O) adapter 620, a sound adapter 630, a network adapter 640, a user interface adapter 650, and a display adapter 660, are operatively coupled to the system bus 602.

A first storage device 622 and a second storage device 624 are operatively coupled to system bus 602 by the I/O adapter 620. The storage devices 622 and 624 can be any of a disk storage device (e.g., a magnetic or optical disk storage device), a solid state magnetic device, and so forth. The storage devices 622 and 624 can be the same type of storage device or different types of storage devices.

A speaker 632 is operatively coupled to system bus 602 by the sound adapter 630. A transceiver 642 is operatively coupled to system bus 602 by network adapter 640. A display device 662 is operatively coupled to system bus 602 by display adapter 660.

A first user input device 652, a second user input device 654, and a third user input device 656 are operatively coupled to system bus 602 by user interface adapter 650. The user input devices 652, 654, and 656 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 652, 654, and 656 can be the same type of user input device or different types of user input devices. The user input devices 652, 654, and 656 are used to input and output information to and from system 600.

Of course, the processing system 600 may also include other elements (not shown), as readily contemplated by one of skill in the art, as well as omit certain elements. For example, various other input devices and/or output devices can be included in processing system 600, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 600 are readily contemplated by one of ordinary skill in the art given the teachings of the present principles provided herein.

Having described preferred embodiments of an ultrasensitive sensor based on a piezoelectric transistor (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A chemical sensor, comprising:
   a functionalized electrode configured to change surface potential in the presence of an analyte;
   a piezoelectric element connected to the functionalized electrode; and
   a piezoresistive element in contact with the piezoelectric element.

2. The chemical sensor of claim 1, further comprising an input terminal and an output terminal in contact with the piezoresistive element.

3. The chemical sensor of claim 2, wherein the output terminal is furthermore in contact with the piezoelectric element, between the piezoelectric element and the piezoresistive element.

4. The chemical sensor of claim 1, wherein the piezoelectric element comprises a piezoelectric material selected from the group consisting of $(1-x)[Pb(Zn_{1/3}Nb_{2/3})O_3]\text{-}x[PbTiO_3]$ and $(1-x)[Pb(Mg_{1/3}Nb_{2/3})O_3]\text{-}x[PbTiO_3]$.

5. The chemical sensor of claim 1, wherein the piezoresistive element comprises a piezoresistive material selected from the group consisting of SmSe, TmTe, and chromium-doped $V_2O_3$.

6. The chemical sensor of claim 1, further comprising a passivating layer configured to hold the piezoresistive element in place through volume changes in the piezoelectric element.

7. The chemical sensor of claim 1, further comprising a sensor analysis system configured to measure a current through the piezoresistive element and to determine a corresponding analyte concentration.

8. The chemical sensor of claim 7, wherein the sensor analysis system is further configured to compare the measured current to a calibration curve of predetermined concentrations of the analyte to determine an analyte concentration that corresponds to the measured current.

9. The chemical sensor of claim 1, wherein the piezoelectric element is configured to change in volume in accordance with the surface potential of the functionalized electrode.

10. The chemical sensor of claim 1, wherein the piezoresistive element is configured to change in resistance in accordance with changes in a volume of the piezoelectric element.

11. A chemical sensor, comprising:
- a functionalized electrode configured to change surface potential in the presence of an analyte;
- a piezoelectric element connected to the functionalized electrode;
- a piezoresistive element in contact with the piezoelectric element; and
- a sensor analysis system configured to measure a current through the piezoresistive element and to compare the measured current to a calibration curve of predetermined concentrations of the analyte to determine an analyte concentration that corresponds to the measured current.

12. The chemical sensor of claim 11, wherein the piezoelectric element comprises a piezoelectric material selected from the group consisting of $(1-x)[Pb(Zn_{1/3}Nb_{2/3})O_3]$-$x[PbTiO_3]$ and $(1-x)[Pb(Mg_{1/3}Nb_{2/3})O_3]$-$x[PbTiO_3]$.

13. The chemical sensor of claim 11, wherein the piezoresistive element comprises a piezoresistive material selected from the group consisting of SmSe, TmTe, and chromium-doped $V_2O_3$.

14. The chemical sensor of claim 11, further comprising a passivating layer configured to hold the piezoresistive element in place through volume changes in the piezoelectric element.

\* \* \* \* \*